United States Patent
Jeong et al.

(10) Patent No.: US 11,778,402 B2
(45) Date of Patent: Oct. 3, 2023

(54) BINAURAL BEAT SOUND OUTPUT DEVICE HAVING IMPROVED SOUND FIELD AND METHOD THEREFOR

(71) Applicant: Dlogixs Co., Ltd, Anyang-Si (KR)

(72) Inventors: In Taek Jeong, Uiwang-Si (KR); Sung Kee Park, Seongnam-Si (KR); Sang Ouk Lee, Seoul (KR); Keun Young Hur, Yongin-Si (KR)

(73) Assignee: Dlogixs Co., Ltd, Anyang-Si (KR)

( * ) Notice: Subject to any disclaimer, the term of this patent is extended or adjusted under 35 U.S.C. 154(b) by 245 days.

(21) Appl. No.: 17/424,980

(22) PCT Filed: Jan. 24, 2019

(86) PCT No.: PCT/KR2019/001008
§ 371 (c)(1),
(2) Date: Jul. 22, 2021

(87) PCT Pub. No.: WO2020/153515
PCT Pub. Date: Jul. 30, 2020

(65) Prior Publication Data
US 2022/0095067 A1     Mar. 24, 2022

(51) Int. Cl.
*H04S 7/00*         (2006.01)
(52) U.S. Cl.
CPC ..................... *H04S 7/30* (2013.01)
(58) Field of Classification Search
None
See application file for complete search history.

(56) References Cited

U.S. PATENT DOCUMENTS

| 6,081,743 A | 6/2000 | Carter et al. |
| 2007/0084473 A1 | 4/2007 | Hewett |
| 2007/0282216 A1* | 12/2007 | Vesely ............... A61B 5/38 600/545 |
| 2011/0060436 A1* | 3/2011 | Gandini ............ H04R 5/027 700/94 |
| 2017/0173296 A1* | 6/2017 | Park ................... A61B 5/4836 |

FOREIGN PATENT DOCUMENTS

| JP | H07-132145 A | 5/1995 |
| JP | 2017-111414 A | 6/2017 |
| KR | 10-2010-0133151 A | 12/2010 |
| KR | 10-2011-0046207 | 5/2011 |
| KR | 10-1406531 B1 | 6/2014 |
| WO | WO 2009/054699 A1 | 4/2009 |

* cited by examiner

*Primary Examiner* — Duc Nguyen
*Assistant Examiner* — Assad Mohammed
(74) *Attorney, Agent, or Firm* — Blank Rome LLP (57) ABSTRACT

The present invention relates to a binaural beat sound output device having an improved sound field and a method therefor and, more specifically, to: a brainwave sound output device using binaural beats, which receives music desired by a user and applies binaural beats to a specific frequency band thereof, so that the device can provide the music through a stereo sound source while inducing a desired brainwave state by the stereo sound source, and thus can improve the sound field without the sense of rejection or monotony to the music; and a method therefor.

12 Claims, 5 Drawing Sheets

SOUND SOURCE DATA BEFORE BEING SHIFTED

SOUND SOURCE DATA AFTER BEING SHIFTED

BINAURAL BEAT SOUND OUTPUT DEVICE HAVING IMPROVED SOUND FIELD AND METHOD THEREFOR

TECHNICAL FIELD

The present invention relates to a binaural beat sound output device having an improved sound field and a method therefor, and more particularly, to a brain wave sound output device using binaural beats capable of having an improved sound field without the sense of rejection to or monotony of music by receiving music desired by a user and applying binaural beats to a specific frequency band to provide a stereo sound source while inducing a desired brain wave state by the stereo sound source.

BACKGROUND ART

It has been known that a human brain emits different frequencies according to each state, and when a signal of a predetermined frequency is continuously received with sound or light from the outside to the human brain, a brain wave also has an effect of synchronizing with an input frequency. In general, when the human brain is meditating, the human mind and body are relaxed, and when a person focuses his/her mind, the human brain is activated.

A binaural beat is the principle of inducing a desired brain wave to the brain using a difference between two frequencies.

That is, the binaural beat refers to a sound generated by modulating input audio signals into sounds in an audio frequency (20 to 20,000 Hz) band that is audible by a person in order to form external waves having an influence on the brain because the person may not perceive low frequencies and effectively combining such sounds with each other so as to have an influence on the brain.

That is, in a case of a sound in a 11 Hz band that belongs to an alpha stage and is an inaudible frequency band that is inaudible by the person, a frequency difference of 1 Hz is given by supplying a sound in a 300 Hz band, which is an audio frequency band, to a left ear of the person, and supplying a sound in a 311 Hz band, which is an audio frequency band, to a right ear of the person using a stereo sound. In this case, the brain combines these two sounds with each other in the brain to accept a difference of 1 Hz, such that a brain wave-induced stimulation is performed.

A human brain wave is an electrical signal generated on a surface of the head, and a source of the human brain wave is a current generated by ions passing through cell membranes of excitatory neurons. The brain wave is measured and psychological states of the person may be decided according to frequency ranges of the measured brain wave, and different psychological states are represented according to each frequency range.

For example, when the frequency range is 0.4 Hz or more and less than 4 Hz, it is a delta wave and represents a very deep sleep state, when the frequency range is 4 to 8 Hz, it is a theta wave and represents a sleep and meditation state, when the frequency range is 8 to 14 Hz, it is an alpha wave and represents a relaxed state, and when the frequency range is 15 to 24 Hz, it is a beta wave and represents a tense state.

As described above, the frequency of the brain represents a psychological state of the person that changes moment by moment, and the binaural beat has been used in order to artificially induce the psychological state of the person based on the study that an actual psychological state of the person changes in a case where the brain wave of the person is changed by forcible brain wave induction.

Conventionally, all signals of the left (L) and the right (R) are processed as mono signals, and binaural beats are then generated through frequency shift for a desired frequency band, such that a user may listen to a sound composed of binaural beats for desired music.

However, inconvenience in listening to the sound has occurred due to a beat phenomenon caused by a frequency shift phenomenon, and a problem that a stereo sense which is essential for listening to the music, completely disappears in a process of converting a stereo audio signal to a mono audio signal and a problem that a sound quality is deteriorated due to a monotonous sound (mono sound) accordingly have also occurred.

In this regard, Korean Patent No. 10-1406531 (entitled "Apparatus and Method for Generating Binaural Beat from Stereo Audio Signal) discloses an apparatus and method capable of preventing distortion of a stereo audio signal while generating binaural beats from the stereo audio signal.

RELATED ART DOCUMENT

Patent Document

Korean Patent No. 10-1406531 (registered on Jun. 3, 2014)

DISCLOSURE

Technical Problem

An object of the present invention is to provide a brain wave sound output device using binaural beats capable of having an improved sound field without the sense of rejection to or monotony of music by receiving music desired by a user and applying binaural beats to a specific frequency band to provide a stereo sound source while inducing a desired brain wave state by the stereo sound source, and a method therefor.

Technical Solution

In one general aspect, a binaural beat sound output device having an improved sound field includes: a sound source input unit 100 receiving sound source data composed of a first stereo sound source signal and a second stereo sound source signal; a mono conversion unit 200 receiving the sound source data and converting the sound source data into a first mono sound source signal to generate the first mono sound source signal; a frequency control unit 300 receiving the first stereo sound source signal, the second stereo sound source signal, and the first mono sound source signal, analyzing frequency bands constituting the first stereo sound source signal, the second stereo sound source signal, and the first mono sound source signal, and shifting a specific frequency band in the frequency band constituting the first mono sound source signal by a predetermined frequency to generate a second mono sound source signal; and an output audio generation unit 400 generating a first stereo output signal by removing the specific frequency band of the first stereo sound source signal and adding the specific frequency band of the first mono sound source signal and generating a second stereo output signal by removing the specific frequency band of the second stereo sound source signal and adding the specific frequency band of the second mono sound source signal.

The binaural beat sound output device having an improved sound field may further include an integrated control unit 500 varying the specific frequency band or the predetermined frequency according to a manipulation of a user or preset mode information.

The specific frequency band may be selected from a frequency band of 500 to 6000 Hz, and the predetermined frequency may be a frequency within any one of frequency ranges of an alpha wave, a beta wave, a theta wave, or a delta wave which is a brain wave to be induced.

The integrated control unit 500 may set the brain wave to be induced according to a manipulation of the user or mode information input from the user, and set a brain wave induction sequence so that the set brain wave is induced.

The binaural beat sound output device having an improved sound field may further include: a brain wave sensor unit 600 including a brain wave sensor sensing a current brain wave state of the user; and a heart rate sensor unit 700 including a heart rate sensor sensing a current heart rate of the user, wherein the integrated control unit 500 receives the current brain wave state of the user sensed by the brain wave sensor unit 600 and determines a brain wave induction sequence so that brain waves are sequentially induced, and receives the current heart rate of the user sensed by the heart rate sensor unit 700 and varies reproduction speeds of the first stereo output signal and the second stereo output signal.

The integrated control unit 500 may receive the current brain wave state of the user sensed by the brain wave sensor unit 600, and control the frequency control unit 300 so that the brain waves are sequentially induced from a state in which a frequency of the brain wave is high to a state to in which a frequency of the brain wave is low or from a state in which a frequency of the brain wave is low to a state to in which a frequency of the brain wave is high, in a brain wave induction sequence from the current brain wave state of the user to the brain wave to be induced.

The binaural beat sound output device having an improved sound field may further include a sound output means 800 converting the first stereo output signal and the second stereo output signal into sounds and output the converted sounds, wherein a sound corresponding to the first stereo output signal is output to one side of the sound output means 800, and a sound corresponding to the second stereo output signal is output to the other side of the sound output means 800.

In another general aspect, a binaural beat sound output method having an improved sound field includes: a sound source receiving step of receiving sound source data stored in advance or input from the outside and composed of a first stereo sound source signal and a second stereo sound source signal, by a sound source input unit; a mono generating step of receiving the sound source data and converting the sound source data into a first mono sound source signal to generate the first mono sound source signal, by a mono conversion unit; a frequency band analyzing step of receiving the first stereo sound source signal, the second stereo sound source signal, and the first mono sound source signal and analyzing frequency bands constituting the first stereo sound source signal, the second stereo sound source signal, and the first mono sound source signal, by a frequency control unit; a frequency shifting step of shifting a specific frequency band in the frequency band constituting the first mono sound source signal by a predetermined frequency to generate a second mono sound source signal, by the frequency control unit; and an output audio generating step of generating a first stereo output signal by removing the specific frequency band of the first stereo sound source signal and adding the specific frequency band of the first mono sound source signal and generating a second stereo output signal by removing the specific frequency band of the second stereo sound source signal and adding the specific frequency band of the second mono sound source signal, by an output audio generation unit, wherein the binaural beat sound output method having an improved sound field further comprises a controlling step of varying the specific frequency band or the predetermined frequency according to a manipulation of a user or preset mode information, by an integrated control unit.

The specific frequency band may be selected from a frequency band of 500 to 6000 Hz, and the predetermined frequency may be a frequency within any one of frequency ranges of an alpha wave, a beta wave, a theta wave, or a delta wave which is a brain wave to be induced.

The controlling step may include a user inputting step of setting the brain wave to be induced according to a manipulation of the user or mode information input from the user and setting a brain wave induction sequence so that the set brain wave is induced.

The binaural beat sound output method having an improved sound field may further include: a brain wave sensing step of sensing a current brain wave state of the user using a brain wave sensor, by the integrated control unit, and a heart rate sensing step of sensing a current heart rate state of the user using a heart rate sensor, by the integrated control unit, wherein the controlling step includes: a brain wave induction sequence determining step of receiving the sensed current brain wave state of the user and determining a brain wave induction sequence so that the brain waves are sequentially induced; and a speed varying step of receiving the sensed current heart rate of the user and varying reproduction speeds of the first stereo output signal and the second stereo output signal.

In the controlling step, the sensed current brain wave state of the user may be received, and the frequency shifting step may be controlled so that the brain waves are sequentially induced from a state in which a frequency of the brain wave is high to a state to in which a frequency of the brain wave is low or from a state in which a frequency of the brain wave is low to a state to in which a frequency of the brain wave is high, in a brain wave induction sequence from the current brain wave state of the user to the brain wave to be induced.

Advantageous Effects

With the binaural beat sound output device having an improved sound field and the method therefor according to the present invention having the configuration as described above, it is possible to provide a stereo sound source while inducing a desired brain wave state by the stereo sound source by receiving music desired by a user and applying binaural beats to a specific frequency band, such that a sound field is improved without the sense of rejection to or monotony of music, thereby making it possible to minimize a beat phenomenon.

In addition, it is possible to suppress sound quality deterioration of a music signal or a learning audio signal to which the binaural beats are applied due to the improved sound field.

BEST MODE

A binaural beat sound output device having an improved sound field and a method therefor according to the present invention will be described in detail with reference to the accompanying drawings. Drawings to be provided below are provided by way of example so that the spirit of the present invention may be sufficiently transferred to those skilled in the art. Therefore, the present invention is not limited to drawings to be provided below, but may be implemented in other forms. In addition, like reference numerals denote like elements throughout the specification.

In this case, technical terms and scientific terms used in the present specification have the meaning understood by those skilled in the art to which the present invention pertains unless otherwise defined, and a description for known functions and configurations unnecessarily obscuring the gist of the present invention will be omitted in the following description and the accompanying drawings.

In addition, a system refers to a set of components including devices, mechanisms, means, and the like, systematized in order to perform required functions and regularly interacting with one another.

A binaural beat sound output device having an improved sound field and a method therefor according to an embodiment of the present invention relate to a device and a method that are capable of inducing music desired by a user to a target brain wave using binaural beats and are capable of improving a sound field by a stereo sound source rather than a mono sound source and providing the stereo sound source without the sense of rejection to or monotony of music without being aware of distortion of a sound source by applying the binaural beats to a specific frequency band of the music.

In particular, it is possible to improve the sound field by providing the stereo sound source, so that a beat phenomenon may be minimized, and it is possible to suppress sound quality deterioration in a process of converting a stereo sound source into a mono sound source.

Figure 1:
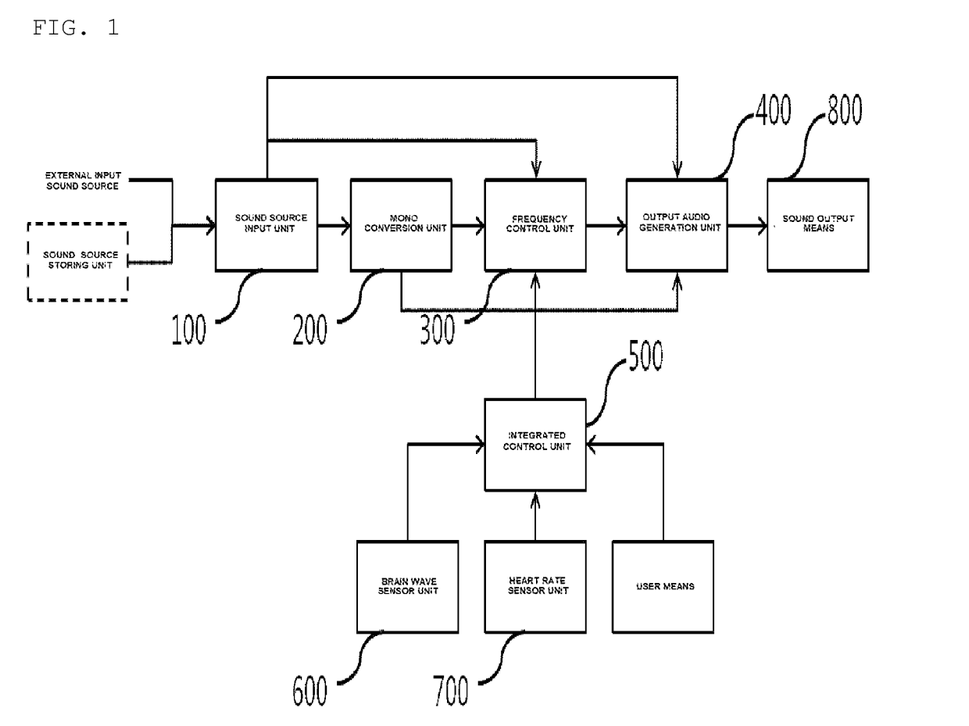
FIG. 1 is a diagram illustrating a configuration of a binaural beat sound output device having an improved sound field according to an embodiment of the present invention.

FIG. 1 is a diagram illustrating a configuration of a binaural beat sound output device having an improved sound field according to an embodiment of the present invention. The binaural beat sound output device having an improved sound field according to an embodiment of the present invention will be described with reference to FIG. 1.

It is preferable that the binaural beat sound output device having an improved sound field according to an embodiment of the present invention is configured to include a sound source input unit 100, a mono conversion unit 200, a frequency control unit 300, an output audio generation unit 400, and an integrated control unit 500.

It is preferable that the respective components operate through a terminal means controlled through one micro controller unit (MCU), but this is only an embodiment of the present invention, and in some cases, the respective components may also operate through terminal means controlled through respective MCUs connected to each other through a wired or wireless network.

The respective components will be described in detail.

It is preferable that the sound source input unit 100 receives sound source data composed of a first stereo sound source signal and a second stereo sound source signal.

It is preferable that the sound source input unit 100 receives a desired external sound source from a user or receives sound source data selected by the user from among sound source data stored in advance in a sound source storing unit.

In this case, the sound source data are generally composed of stereo sound sources, and it is thus preferable that the sound source data are composed of the first stereo sound source signal and the second stereo sound source signal without a separate conversion process.

In addition, in a case where the sound source input unit 100 receives the external sound source from the user, it is preferable that the sound source input unit 100 converts the external sound source input as an analog signal into a digital signal using an analog-to-digital converter (ADC).

It is preferable that the mono conversion unit 200 receives the sound source data and converts the sound source data into a mono sound source to generate a first mono sound source signal.

That is, it is preferable that the mono conversion unit 200 generates the first mono sound source signal by extracting a mono sound source from the sound source data, which is the stereo sound source.

In this case, the mono sound source may be any one of left or right sound source components of a stereo audio component or be one mono sound source extracted by mixing stereo components with each other.

It is preferable that the frequency control unit 300 analyzes frequency bands constituting each of the first stereo sound source signal and the second stereo sound source signal received from the sound source input unit 100 and the first mono sound source signal received from the mono conversion unit 200. In this case, the analysis of the frequency bands means obtaining frequency components constituting each of the first and second stereo sound source signals and the first mono sound source signal formed by performing a Fourier transform on each of the first and second stereo sound source signals and the first mono sound source signal.

In addition, it is preferable that the frequency control unit 300 extracts a specific frequency band in the frequency band constituting the first mono sound source signal and shifts the extracted specific frequency band by a predetermined frequency to generate a second mono sound source signal, and it is most preferable that the frequency shift is implemented using a digital signal processor (DSP).

It is preferable that the frequency control unit 300 of the binaural beat sound output device having an improved sound field according to an embodiment of the present invention varies and sets the specific frequency band or the predetermined frequency according to a manipulation of the user or preset mode information under the control of the integrated control unit 500 to generate the second mono sound source signal. That is, the frequency control unit 300 may set a frequency band and a frequency amount to be shifted in consideration of a frequency of a brain wave to be induced under the control of the integrated control unit 500, and shift the set frequency band in the frequency band constituting the first mono sound source signal by the set frequency amount to generate the second mono sound source signal.

In detail, it is preferable that the integrated control unit 500 sets a brain wave to be induced by applying binaural beats according to a manipulation of the user or mode information (desired brain wave state information) input from the user and sets a brain wave induction sequence so that the set brain wave (brain wave to be induced) is induced.

To this end, as illustrated in FIG. 1, it is preferable that the binaural beat sound output device having an improved sound field according to an embodiment of the present invention is configured to further include a brain wave sensor unit 600 and a heart rate sensor unit 700.

It is preferable that the brain wave sensor unit 600 is configured to include a brain wave sensor sensing a current brain wave state of the user, and the heart rate sensor unit 700 is configured to include a heart rate sensor sensing a current heart rate of the user.

The brain wave sensor unit 600 may be implemented in the form of a hair band or an attachment pin so as to be able to be in contact with a user's head, or may be included as a separate component in a headphone.

The heart rate sensor unit 700 may be implemented as a wristband so as to be able to be attached to a user's wrist or may be implemented in the form of a general electrode attached to a user's chest or neck.

It is preferable that the integrated control unit 500 receives the current brain wave state of the user sensed by the brain wave sensor unit 600 and determines a brain wave induction sequence for sequentially inducing the current brain wave state to a brain wave set according to the manipulation of the user or the mode information received from the user.

In detail, it is preferable that the integrated control unit 500 receives the current brain wave state of the user sensed by the brain wave sensor unit 600, and controls the frequency control unit 300 so that the brain waves are sequentially induced from a state in which a frequency of the brain wave is high to a state to in which a frequency of the brain wave is low or from a state in which a frequency of the brain wave is low to a state to in which a frequency of the brain wave is high, in the brain wave induction sequence from the current brain wave state of the user to a target brain wave set according to the manipulation of the user or the mode information input from the user.

The brain wave induction sequence refers to a brain wave induction sequence from the current brain wave state of the user sensed by the brain wave sensor unit 600 to the target brain wave desired by the user, and it is preferable to control the frequency control unit 300 to induce the brain waves in a sequence of sequentially increasing the frequency of the brain wave (delta wave-theta wave-alpha wave-beta wave) or decreasing the frequency of the brain wave (beta wave-alpha wave-theta wave-delta wave).

Through this, it is possible to naturally transition from the current brain wave state to the target brain wave state.

Figure 3:
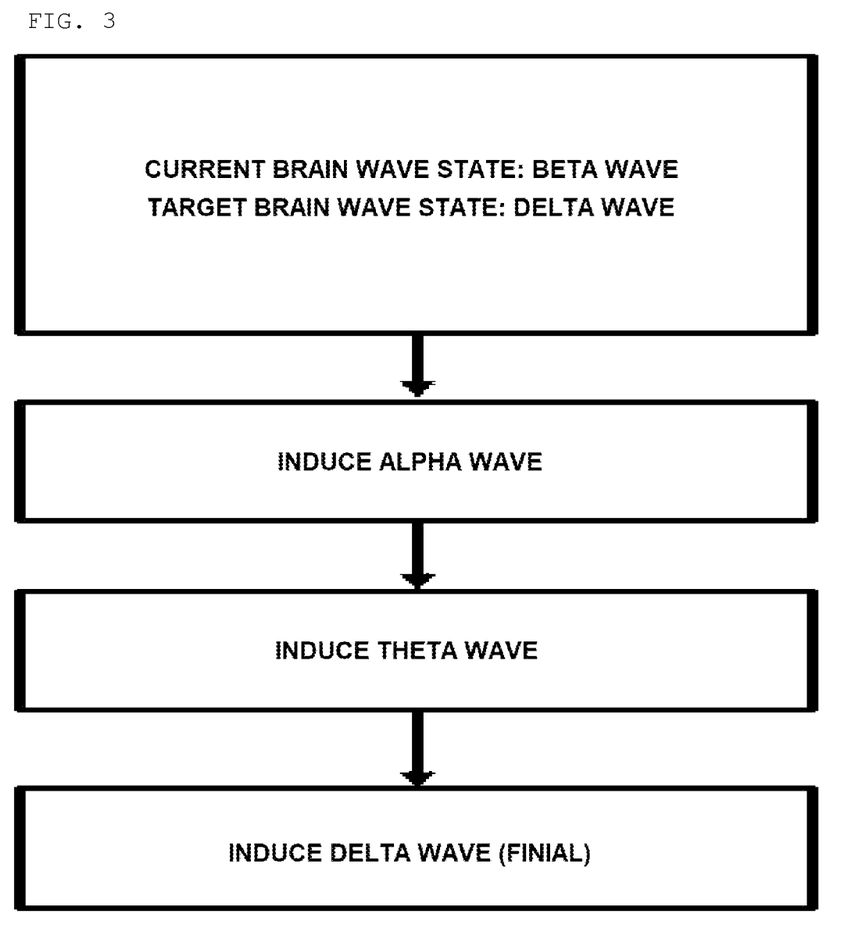
FIG. 3 is illustrating a brain wave induction sequence to a brain wave to be induced in the binaural beat sound output device having an improved sound field and the method therefor according to an embodiment of the present invention.

For example, as illustrated in FIG. 3, in a case where the current brain wave state of the user is a beta wave and the target brain wave state desired by the user is a delta wave, the integrated control unit 500 does not control the frequency control unit 300 to directly induce a delta wave state in the frequency shift, but may control the frequency control unit 300 to induce a delta wave state through a beta wave-alpha wave-theta wave.

On the contrary, in a case where the current brain wave state of the user is a theta wave and the target brain wave state desired by the user is a beta wave, the integrated control unit 500 may control the frequency control unit 300 to induce a beta wave state through a theta wave-alpha wave in the frequency shift.

In addition, it is preferable that the integrated control unit 500 receives the current heart rate of the user sensed by the heart rate sensor unit 700 and varies and controls reproduction speeds of a first stereo output signal and a second stereo output signal. That is, in a case where the user is stable and the current heart rate becomes slow, it is preferable to slowly reproduce an audio to help to induce a brain wave state of the user to the delta wave state.

The first stereo output signal and the second stereo output signal will be described later.

As described above, it is preferable that the frequency control unit 300 varies and sets the specific frequency band or the predetermined frequency according to the control of the integrated control unit 500 to generate the second mono sound source signal.

In more detail, it has been known that a discrimination limitation of human hearing for a frequency change at 500 to 6000 Hz is 0.3%. That is, in a frequency range between 500 and 6000 Hz, a human hearing ability may discriminate a frequency change of 1.5 to 18 Hz, and in a case where the frequency is shifted using binaural beats, when the frequency is shifted by 0.3% or more in the frequency range between 500 and 6000 Hz, the user recognizes a change in sound quality.

Therefore, in the binaural beat sound output device having an improved sound field according to an embodiment of the present invention, it is preferable to set a lower limit of the frequency band to be shifted to a value within 0.3% so that the user may not recognize the change in sound quality of the sound source even by the frequency shift.

For example, the frequency band and the frequency amount to be shifted are associated with the frequency of the brain wave to be induced. In a case where it is intended to induce an alpha wave, since the alpha wave has a frequency range of 8 to 14 Hz as described above, it is preferable that a frequency amount to be shifted using the binaural beats is set in a frequency band within the range of 8 to 14 Hz, and it is preferable that a lower limit value of the frequency band to be shifted is set to a value within the range of 8 to 14/0.3%, that is, 2667 to 4667 Hz.

The following Table 1 relates to a target brain wave to be induced by the user by using the binaural beat sound output device having an improved sound field according to an embodiment of the present invention and a preferable frequency amount to be shifted and a preferable lower limit of a frequency band to be shifted according to the target brain wave.

TABLE 1

| Brain wave state to be induced (Target brain wave state) | | | Lower limit of |
| --- | --- | --- | --- |
| Brain wave state | Frequency | Frequency amount | frequency band to be shifted |
| Delta wave | 0.4 to 4 Hz | 0.4 to 4 Hz | 133 to 1333 Hz |
| Theta wave | 4 to 8 Hz | 4 to 8 Hz | 1333 to 2667 Hz |
| Alpha wave | 8 to 14 Hz | 8 to 14 Hz | 2667 to 4667 Hz |
| Beta wave | 15 to 24 Hz | 15 to 24 Hz | 5000 to 8000 Hz |

As described above, it is preferable that the integrated control unit 500 sets the frequency band to be shifted and the frequency amount to be shifted among the frequency components constituting the first mono sound source signal with reference to values represented in the above Table 1 in order to generate a sound source signal for inducing a brain wave (target brain wave state) to be induced set according to the manipulation of the user or the mode information (desired brain wave state information) input from the user.

The frequency control unit 300 generates the second mono sound source signal by shifting a frequency of the first mono sound source signal according to a setting of the integrated control unit 500.

In addition, in this case, the binaural beat sound output device having an improved sound field according to an embodiment of the present invention does not provide a mono sound source, but transfers a stereo sound source to improve the sound field, thereby making it possible to suppress the beat phenomenon and the sound quality deterioration, as described above.

To this end, it is preferable to remove a specific frequency band for the first stereo sound source signal and the second stereo sound source signal and mix only corresponding portions with the first mono sound source signal before the shift and the second mono sound source signal after the shift, respectively, through the output audio generation unit 400.

In detail, it is preferable that the output audio generation unit 400 generates the first stereo output signal by removing the specific frequency band of the first stereo sound source signal and adding the specific frequency band of the first mono sound source signal, and generates the second stereo output signal by removing the specific frequency band of the second stereo sound source signal and adding the specific frequency band of the second mono sound source signal.

The first stereo output signal and the second stereo output signal generated through the output audio generation unit 400 may induce the brain wave state desired by the user without the sense of rejection or monotony, without distortion of the sound source or the sound quality deterioration, while inducing the desired brain wave state by applying the binaural beats of the mono sound sources only to the specific frequency band of the sound source signals without changing the received stereo source sources, as described above.

Figure 2:
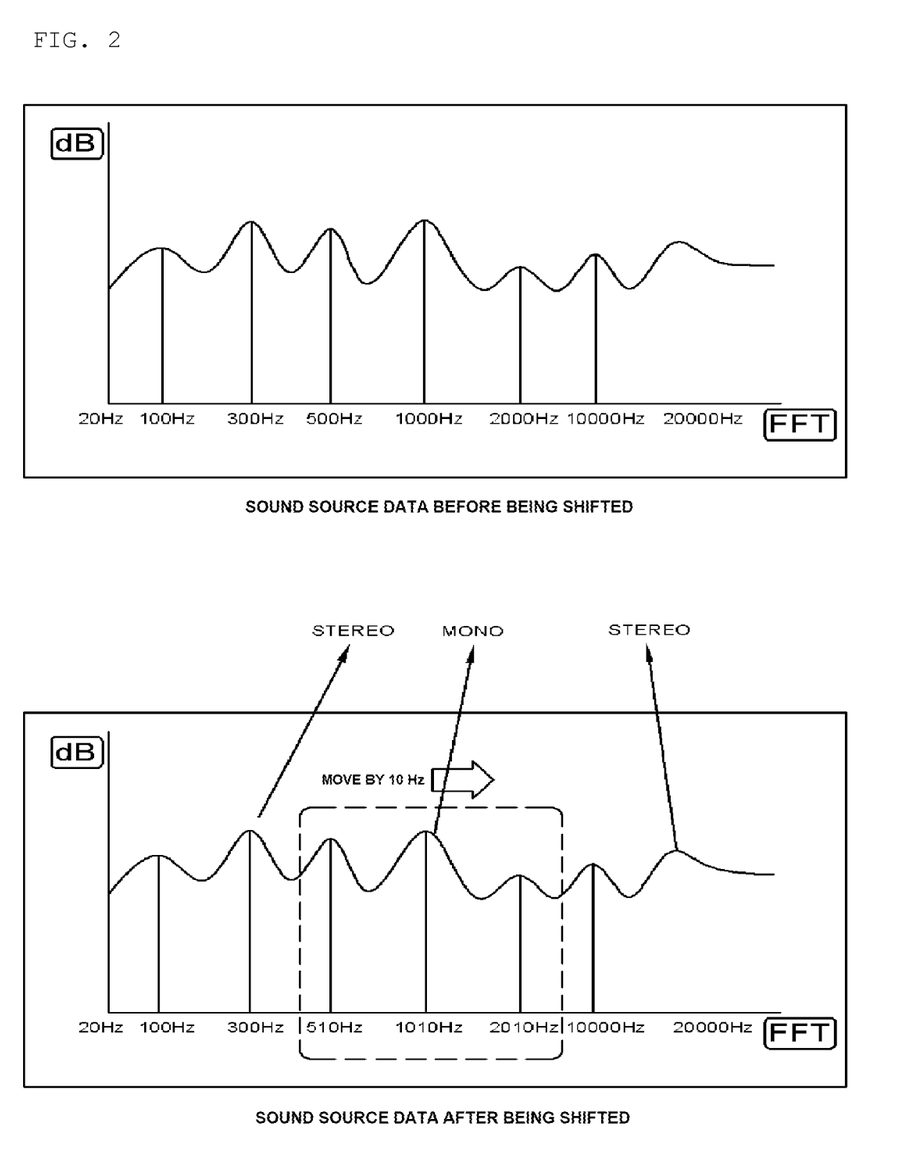
FIG. 2 is a view illustrating frequency band spectra of a sound source signal in the binaural beat sound output device having an improved sound field and a method therefor according to an embodiment of the present invention.

FIG. 2 is a view illustrating frequency band spectra before and after the shift by the binaural beat sound output device having an improved sound field according to an embodiment of the present invention.

In detail, in a case where the brain wave to be induced set according to the manipulation of the user or the mode information (desired brain wave state information) input from the user by the integrated control unit 500 is the alpha wave, when the frequency amount to be shifted is set to 10 Hz and the frequency band to be shifted is set to 500 to 2000 Hz in order to induce the user's brain wave into the alpha wave, a frequency band between 500 and 2000 Hz of the first mono sound source signal is shifted by 10 Hz by the frequency control unit 300 to move to 510 to 2010 Hz, thereby generating the second mono sound source signal.

Here, the frequency band to be shifted is set to 500 to 2000 Hz, but this is only an embodiment of the present invention, and referring to the above Table 1, in a case where the frequency amount to be shifted is set to 10 Hz in order to induce the alpha wave, a lower limit of the frequency band to be shifted may be set to 3333 Hz, and the frequency shift may be performed for a band of 3333 Hz or more.

In this case, the output audio generation unit 400 mixes one of the first or second stereo sound source signal with the first mono sound source signal in the set frequency band, and mixes the other of the first or second stereo sound source signal with the second mono sound source signal in the set frequency band, thereby making it possible to smoothly perform the induction to the desired brain wave while providing the stereo sound source to the user.

It is preferable that the binaural beat sound output device having an improved sound field according to an embodiment of the present invention is configured to further include a sound output means 800.

The sound output means 800 may convert the first stereo output signal and the second stereo output signal into sounds and output the converted sounds.

In detail, it is preferable that a sound corresponding to the first stereo output signal is output to one side of the sound output means 800, and a sound corresponding to the second stereo output signal is output to the other side of the sound output means 800, and the sound output means 800 may be implemented as an audio amplifier for driving a headphone, an earphone or the like connected thereto.

In addition, it is preferable that the binaural beat sound output device having an improved sound field according to an embodiment of the present invention is configured to further include a user means, as illustrated in FIG. 1.

It is preferable to receive a manipulation command (a direct input of the desired brain wave state or a mode input of the brain wave state) of the user or display a current brain wave state, a target brain wave to be induced according to the brain wave state and the manipulation command, and a brain wave induction sequence in progress are displayed, through the user means.

Figure 4:
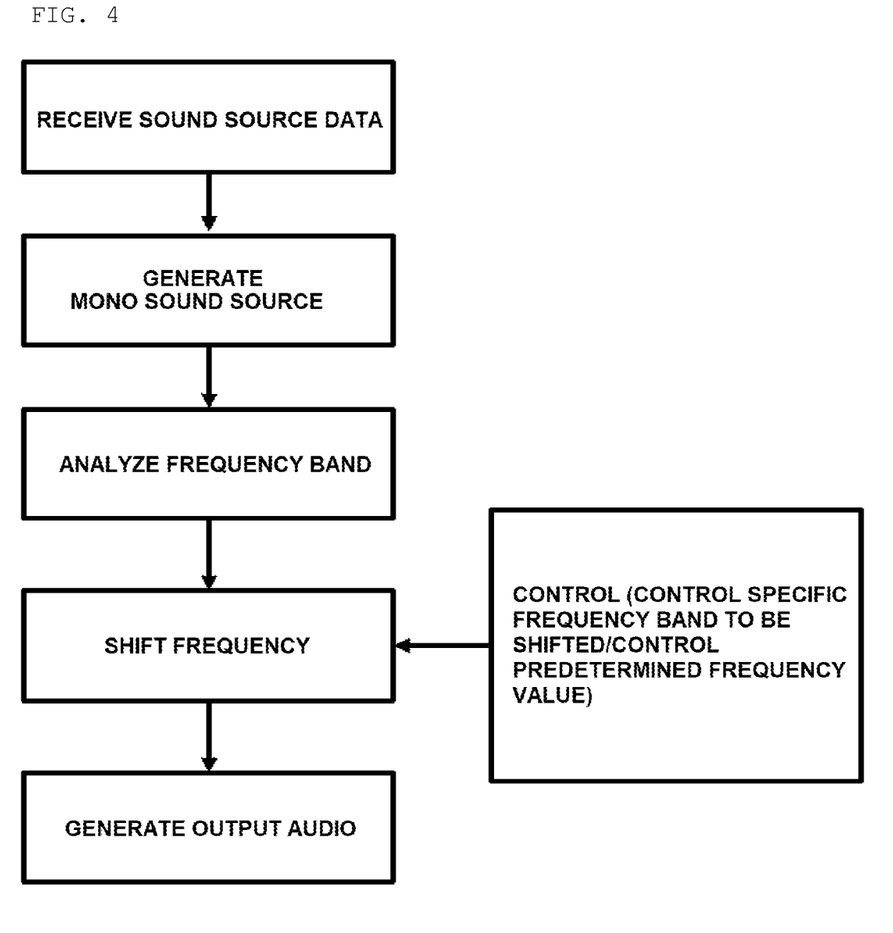
FIGS. 4 and 5 are flowcharts illustrating a binaural beat sound output method having an improved sound field according to an embodiment of the present invention.
Figure 5:
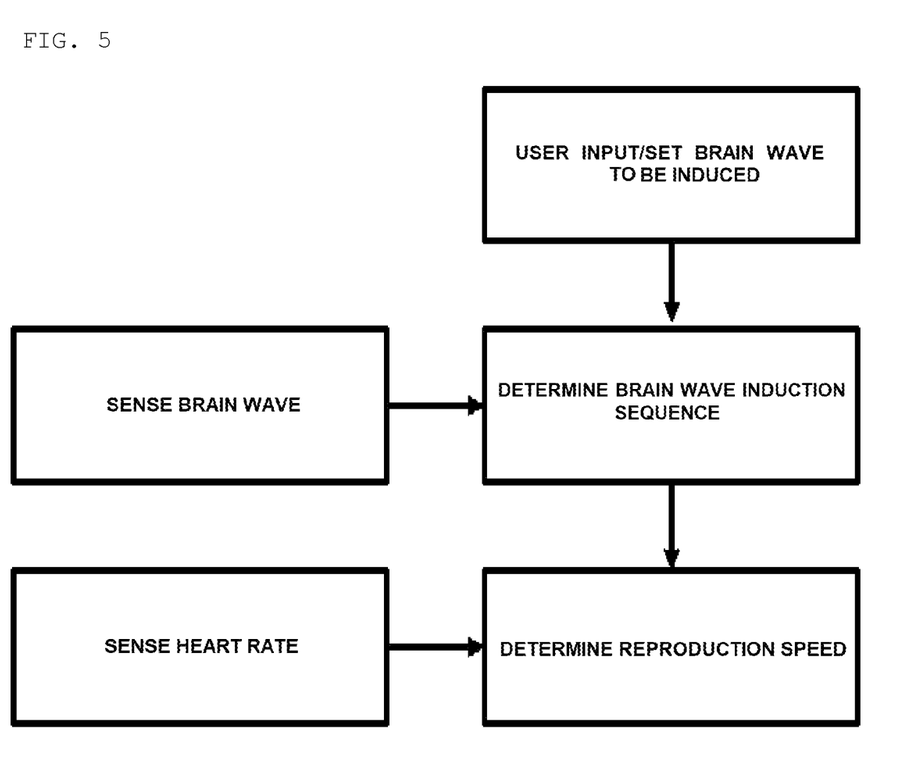

FIGS. 4 and 5 are flowcharts illustrating a binaural beat sound output method having an improved sound field according to an embodiment of the present invention. The binaural beat sound output method having an improved sound field according to an embodiment of the present invention will be described with reference to FIGS. 4 and 5.

It is preferable that the binaural beat sound output method having an improved sound field according to an embodiment of the present invention is configured to include a sound source receiving step, a mono generating step, a frequency band analyzing step, a frequency shifting step, and an output audio generating step, as illustrated in FIG. 4, and it is preferable to control the frequency shifting step through a controlling step.

The respective steps will be described in detail.

In the sound source receiving step, the sound source input unit 100 may receive the sound source data stored in advance or input from the outside and composed of the first stereo sound source signal and the second stereo sound source signal.

In detail, in the sound source receiving step, it is preferable to receive a desired external sound source from the user or receive sound source data selected by the user from among sound source data stored in advance in the sound source storing unit.

In this case, the sound source data are generally composed of stereo sound sources, and it is thus preferable that the sound source data are composed of the first stereo sound source signal and the second stereo sound source signal without a separate conversion process.

In addition, in a case of receiving the external sound source from the user, it is preferable to convert the external sound source input as an analog signal into a digital signal using an analog-to-digital converter (ADC).

In the mono generating step, the mono conversion unit 200 may receive the sound source data and convert the sound source data into the first mono sound source signal to generate the first mono sound source signal.

In detail, in the mono generating step, it is preferable to generate the first mono sound source signal by extracting a mono sound source from the sound source data, which is the stereo sound source.

In this case, the mono sound source may be any one of left or right sound source components of a stereo audio component or be one mono sound source extracted by mixing stereo components with each other.

In the frequency band analyzing step, the frequency control unit 300 may receive the first stereo sound source signal, the second stereo sound source signal, and the first mono sound source signal, and analyze frequency bands constituting the first stereo sound source signal, the second stereo sound source signal, and the first mono sound source signal. In this case, the analysis of the frequency bands means obtaining frequency components constituting each of the first and second stereo sound source signals and the first mono sound source signal formed by performing a Fourier transform on each of the first and second stereo sound source signals and the first mono sound source signal.

In the frequency shifting step, the frequency control unit 300 may shift a specific frequency band in the frequency band constituting the first mono sound source signal by a predetermined frequency to generate a second mono sound source signal.

That is, in the frequency shifting step, it is preferable to extract a specific frequency band in the frequency band constituting the first mono sound source signal and shift the extracted specific frequency band by a predetermined frequency to generate a second mono sound source signal, and it is most preferable that the frequency shift is implemented using a digital signal processor (DSP).

In this case, as described above, in the frequency shifting step, it is preferable that the specific frequency band or the predetermined frequency is varied according to the control of the controlling step.

To this end, in the controlling step, the integrated control unit 500 may vary and set the specific frequency band or the predetermined frequency according to the manipulation of the user or the preset mode information.

In detail, in the frequency shifting step, it is preferable to vary and set the specific frequency band or the predetermined frequency according to the manipulation of the user or the preset mode information under the control of the controlling step to generate the second mono sound source signal. That is, in the frequency shifting step, a frequency band and a frequency amount to be shifted may be set in consideration of a frequency of a brain wave to be induced under the control of the controlling step, and the set frequency band in the frequency band constituting the first mono sound source signal may be shifted by the set frequency amount to generate the second mono sound source signal.

In addition, in the controlling step, it is preferable that the integrated control unit 500 sets a brain wave to be induced by applying binaural beats according to a manipulation of the user or mode information (desired brain wave state information) input from the user and sets a brain wave induction sequence so that the set brain wave (brain wave to be induced) is induced.

To this end, the controlling step may be configured to include a user inputting step of setting the brain wave to be induced according to the manipulation of the user or the mode information input from the user and setting the brain wave induction sequence so that the set brain wave is induced, as illustrated in FIG. 5.

In addition, the binaural beat sound output method having an improved sound field according to an embodiment of the present invention may be configured to further include a brain wave sensing step of sensing a current brain wave state of the user using a brain wave sensor; and a heart rate sensing step of sensing a current heart rate state of the user using a heart rate sensor, in order to decide a current state of the user to set the most appropriate brain wave induction sequence.

Through this, the controlling step may be configured to include a brain wave induction sequence determining step of receiving the sensed current brain wave state of the user and determining the brain wave induction sequence so that the brain waves are sequentially induced.

Through such steps, in the controlling step, it is preferable to receive the sensed current brain wave state of the user and determine the brain wave induction sequence so that the brain waves are sequentially induced to the brain wave set according to the manipulation of the user or the mode information input from the user.

In detail, in the controlling step, it is preferable to receive the sensed current brain wave state of the user, and control the frequency shifting step so that the brain waves are sequentially induced from a state in which a frequency of the brain wave is high to a state to in which a frequency of the brain wave is low or from a state in which a frequency of the brain wave is low to a state to in which a frequency of the brain wave is high, in the brain wave induction sequence from the current brain wave state of the user to the target brain wave set according to the manipulation of the user or the mode information input from the user.

In the controlling step, it is preferable to receive the current brain wave state of the user sensed by the brain wave sensing step, and control the frequency shifting step so that the brain waves are sequentially induced from a state in which a frequency of the brain wave is high to a state to in which a frequency of the brain wave is low or from a state in which a frequency of the brain wave is low to a state to in which a frequency of the brain wave is high, in the brain wave induction sequence from the current brain wave state of the user to the target brain wave set according to the manipulation of the user or the mode information input from the user.

In this case, the brain wave induction sequence refers to a brain wave induction sequence from the current brain wave state of the user sensed by the brain wave sensing step to the target brain wave desired by the user, and it is preferable to control the frequency shifting step to induce the brain waves in a sequence of sequentially increasing the frequency of the brain wave (delta wave-theta wave-alpha wave-beta wave) or decreasing the frequency of the brain wave (beta wave-alpha wave-theta wave-delta wave).

Through this, it is possible to naturally transition from the current brain wave state to the target brain wave state.

For example, as illustrated in FIG. 3, in a case where the current brain wave state of the user is a beta wave and the target brain wave state desired by the user is a delta wave, in the controlling step, the frequency shifting step is not controlled to directly induce a delta wave state in the frequency shift, but the frequency shifting step may be controlled to induce a delta wave state through a beta wave-alpha wave-theta wave.

On the contrary, in a case where the current brain wave state of the user is a theta wave and the target brain wave state desired by the user is a beta wave, in the controlling step, it is preferable to control the frequency shifting step to induce a beta wave state through a theta wave-alpha wave in the frequency shift.

In addition, it is preferable that the controlling step further includes a speed varying step of receiving the sensed current heart rate of the user and varying and controlling reproduction speeds of a first stereo output signal and a second stereo output signal, as illustrated in FIG. 5. That is, in a case where the user is stable and the current heart rate becomes slow, it is preferable to slowly reproduce an audio to help to induce a brain wave state of the user to the delta wave state.

As described above, it is preferable to vary and set the specific frequency band or the predetermined frequency of the frequency shifting step through the controlling step to generate the second mono sound source signal.

In more detail, it has been known that a discrimination limitation of human hearing for a frequency change at 500 to 6000 Hz is 0.3%. That is, in a frequency range between 500 and 6000 Hz, a human hearing ability may discriminate a frequency change of 1.5 to 18 Hz, and in a case where the frequency is shifted using binaural beats, when the frequency is shifted by 0.3% or more in the frequency range between 500 and 6000 Hz, a change in sound quality is recognized.

Therefore, in the binaural beat sound output method having an improved sound field according to an embodiment of the present invention, it is preferable to set a lower limit of the frequency band to be shifted to a value within 0.3% so that the user may not recognize the change in sound quality of the sound source even by the frequency shift.

For example, the frequency band and the frequency amount to be shifted are associated with the frequency of the brain wave to be induced. In a case where it is intended to induce an alpha wave, since the alpha wave has a frequency range of 8 to 14 Hz as described above, it is preferable that a frequency amount to be shifted using the binaural beats is set in a frequency band within the range of 8 to 14 Hz, and it is preferable that a lower limit value of the frequency band to be shifted is set to a value within the range of 8 to 14/0.3%, that is, 2667 to 4667 Hz.

Through this, in the controlling step, it is preferable to set the frequency band to be shifted and the frequency amount to be shifted among the frequency components constituting the first mono sound source signal with reference to values represented in the above Table 1 in order to generate a sound source signal for inducing a brain wave (target brain wave state) to be induced set according to the manipulation of the user or the mode information (desired brain wave state information) input from the user.

In the frequency shifting step, the second mono sound source signal is generated by shifting a frequency of the first mono sound source signal according to a control setting of the controlling step.

In addition, in the binaural beat sound output method having an improved sound field according to an embodiment of the present invention, a mono sound source is not provided, but a stereo sound source is transferred to improve the sound field, thereby making it possible to suppress the beat phenomenon and the sound quality deterioration.

To this end, it is preferable to remove a specific frequency band for the first stereo sound source signal and the second stereo sound source signal and mix only corresponding portions with the first mono sound source signal before the shift and the second mono sound source signal after the shift, respectively, through the output audio generating step.

In detail, in the output audio generating step, it is preferable that the output audio generation unit 400 generates the first stereo output signal by removing the specific frequency band of the first stereo sound source signal and adding the specific frequency band of the first mono sound source signal, and generates the second stereo output signal by removing the specific frequency band of the second stereo sound source signal and adding the specific frequency band of the second mono sound source signal.

The first stereo output signal and the second stereo output signal may induce the brain wave state desired by the user without the sense of rejection or monotony, without distortion of the sound source or the sound quality deterioration, while inducing the desired brain wave state by applying the binaural beats of the mono sound sources only to the specific frequency band of the sound source signals without changing the received stereo source sources, as described above.

FIG. 2 is a view illustrating frequency band spectra before and after the shift by the binaural beat sound output method having an improved sound field according to an embodiment of the present invention.

In a case where the brain wave to be induced set according to the manipulation of the user or the mode information (desired brain wave state information) input from the user by the controlling step is the alpha wave, when the frequency amount to be shifted is set to 10 Hz and the frequency band to be shifted is set to 500 to 2000 Hz in order to induce the user's brain wave into the alpha wave, a frequency band between 500 and 2000 Hz of the first mono sound source signal is shifted by 10 Hz through the frequency shifting step to move to 510 to 2010 Hz, thereby generating the second mono sound source signal.

Here, the frequency band to be shifted is set to 500 to 2000 Hz, but this is only an embodiment of the present invention, and referring to the above Table 1, in a case where the frequency amount to be shifted is set to 10 Hz in order to induce the alpha wave, a lower limit of the frequency band to be shifted may be set to 3333 Hz, and the frequency shift may be performed for a band of 3333 Hz or more.

In this case, one of the first or second stereo sound source signal is mixed with the first mono sound source signal in the set frequency band and the other of the first or second stereo sound source signal is mixed with the second mono sound source signal in the set frequency band, by the output audio generating step, thereby making it possible to smoothly perform the induction to the desired brain wave while providing the stereo sound source to the user.

In addition, the first stereo output signal and the second stereo output signal generated by the output audio generating step may be converted into sounds, and the converted sounds may be output through the sound output means 800.

In detail, it is preferable that a sound corresponding to the first stereo output signal is output to one side of the sound output means 800, and a sound corresponding to the second stereo output signal is output to the other side of the sound output means 800, and the sound output means 800 may be implemented as an audio amplifier for driving a headphone, an earphone or the like connected thereto.

In the binaural beat sound output method having an improved sound field according to an embodiment of the present invention, a progress state (progress situation) of each step may be transferred to the user means or input information of the user may be received.

It is preferable to receive a manipulation command (a direct input of the desired brain wave state or a mode input of the brain wave state) of the user or display a current brain wave state, a target brain wave to be induced according to the brain wave state and the manipulation command, and a brain wave induction sequence in progress are displayed, through the user means.

In other words, in the binaural beat sound output device having an improved sound field and the method therefor according to an embodiment of the present invention, it is possible to induce the brain wave state desired by the user without the sense of rejection or the monotony, without distortion of the sound source or the sound quality deterioration, while inducing the desired brain wave state by applying the binaural beats of the mono sound sources only to the specific frequency band of the sound source signals without changing the received stereo source sources.

Hereinabove, although the present invention has been described by specific matters such as detailed components, exemplary embodiments, and the accompanying drawings, they have been provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to these exemplary embodiments, but the claims and all of modifications equal or equivalent to the claims are intended to fall within the scope and spirit of the present invention.

DETAILED DESCRIPTION OF MAIN ELEMENTS

100: sound source input unit
200: mono conversion unit
300: frequency control unit
400: output audio generation unit
500: integrated control unit
600: brain wave sensor unit
700: heart rate sensor unit
800: sound output means

The invention claimed is:

1. A binaural beat sound output device having an improved sound field, comprising:
a sound source input unit 100 receiving sound source data composed of a first stereo sound source signal and a second stereo sound source signal;
a mono conversion 200 receiving the sound source data and converting the sound source data into a first mono sound source signal to generate the first mono sound source signal;
a frequency control unit 300 receiving the first stereo sound source signal, the second stereo sound source signal, and the first mono sound source signal, analyzing frequency bands constituting the first stereo sound source signal, the second stereo sound source signal, and the first mono sound source signal, and shifting a specific frequency band in the frequency band constituting the first mono sound source signal by a predetermined frequency to generate a second mono sound source signal; and
an output audio generation 400 generating a first stereo output signal by removing the specific frequency band of the first stereo sound source signal and adding the specific frequency band of the first mono sound source signal and generating a second stereo output signal by removing the specific frequency band of the second stereo sound source signal and adding the specific frequency band of the second mono sound source signal.

2. The binaural beat sound output device having an improved sound field of claim 1, further comprising an integrated control unit 500 varying the specific frequency band or the predetermined frequency according to a manipulation of a user or preset mode information.

3. The binaural beat sound output device having an improved sound field of claim 2, wherein the specific frequency band is selected from a frequency band of 500 to 6000 Hz, and
the predetermined frequency is a frequency within any one of frequency ranges of an alpha wave, a beta wave, a theta wave, or a delta wave which is a brain wave to be induced.

4. The binaural beat sound output device having an improved sound field of claim 3, wherein the integrated control unit 500
sets the brain wave to be induced according to a manipulation of the user or mode information input from the user, and
sets a brain wave induction sequence so that the set brain wave is induced.

5. The binaural beat sound output device having an improved sound field of claim 4, further comprising:
a brain wave sensor unit 600 including a brain wave sensor sensing a current brain wave state of the user; and
a heart rate sensor unit 700 including a heart rate sensor sensing a current heart rate of the user,
wherein the integrated control unit 500
receives the current brain wave state of the user sensed by the brain wave sensor unit 600 and determines a brain wave induction sequence so that brain waves are sequentially induced, and
receives the current heart rate of the user sensed by the heart rate sensor unit 700 and varies reproduction speeds of the first stereo output signal and the second stereo output signal.

6. The binaural beat sound output device having an improved sound field of claim 5, wherein the integrated control unit 500 receives the current brain wave state of the user sensed by the brain wave sensor unit 600, and controls the frequency control unit 300 so that the brain waves are sequentially induced from a state in which a frequency of the brain wave is high to a state to in which a frequency of the brain wave is low or from a state in which a frequency of the brain wave is low to a state to in which a frequency of the brain wave is high, in a brain wave induction sequence from the current brain wave state of the user to the brain wave to be induced.

7. The binaural beat sound output device having an improved sound field of claim 1, further comprising a sound output means 800 converting the first stereo output signal and the second stereo output signal into sounds and output the converted sounds,
wherein a sound corresponding to the first stereo output signal is output to one side of the sound output means 800, and a sound corresponding to the second stereo output signal is output to the other side of the sound output means 800.

8. A binaural beat sound output method having an improved sound field, comprising:
a sound source receiving step of receiving sound source data stored in advance or input from the outside and composed of a first stereo sound source signal and a second stereo sound source signal, by a sound source input unit;

a mono generating step of receiving the sound source data and converting the sound source data into a first mono sound source signal to generate the first mono sound source signal, by a mono conversion unit;

a frequency band analyzing step of receiving the first stereo sound source signal, the second stereo sound source signal, and the first mono sound source signal and analyzing frequency bands constituting the first stereo sound source signal, the second stereo sound source signal, and the first mono sound source signal, by a frequency control unit;

a frequency shifting step of shifting a specific frequency band in the frequency band constituting the first mono sound source signal by a predetermined frequency to generate a second mono sound source signal, by the frequency control unit; and an output audio generating step of generating a first stereo output signal by removing the specific frequency band of the first stereo sound source signal and adding the specific frequency band of the first mono sound source signal and generating a second stereo output signal by removing the specific frequency band of the second stereo sound source signal and adding the specific frequency band of the second mono sound source signal, by an output audio generation unit, wherein the binaural beat sound output method having an improved sound field further comprises a controlling step of varying the specific frequency band or the predetermined frequency according to a manipulation of a user or preset mode information, by an integrated control unit.

9. The binaural beat sound output method having an improved sound field of claim 8, wherein the specific frequency band is selected from a frequency band of 500 to 6000 Hz, and the predetermined frequency is a frequency within any one of frequency ranges of an alpha wave, a beta wave, a theta wave, or a delta wave which is a brain wave to be induced.

10. The binaural beat sound output method having an improved sound field of claim 9, wherein the controlling step includes a user inputting step of setting the brain wave to be induced according to a manipulation of the user or mode information input from the user and setting a brain wave induction sequence so that the set brain wave is induced.

11. The binaural beat sound output method having an improved sound field of claim 10, further comprising:

a brain wave sensing step of sensing a current brain wave state of the user using a brain wave sensor, by the integrated control unit, and a heart rate sensing step of sensing a current heart rate state of the user using a heart rate sensor, by the integrated control unit, wherein the controlling step includes:

a brain wave induction sequence determining step of receiving the sensed current brain wave state of the user and determining a brain wave induction sequence so that the brain waves are sequentially induced; and a speed varying step of receiving the sensed current heart rate of the user and varying reproduction speeds of the first stereo output signal and the second stereo output signal.

12. The binaural beat sound output method having an improved sound field of claim 11, wherein in the controlling step, the sensed current brain wave state of the user is received, and the frequency shifting step is controlled so that the brain waves are sequentially induced from a state in which a frequency of the brain wave is high to a state to in which a frequency of the brain wave is low or from a state in which a frequency of the brain wave is low to a state to in which a frequency of the brain wave is high, in a brain wave induction sequence from the current brain wave state of the user to the brain wave to be induced.

\* \* \* \* \*